United States Patent [19]

Hecox et al.

[11] Patent Number: 4,813,430

[45] Date of Patent: Mar. 21, 1989

[54] MICROPHONIC PROBE TUBE MOUNTING FOR REAL EAR MEASUREMENTS

[75] Inventors: Kurt E. Hecox; Paul A. Schmitt, both of Madison, Wis.

[73] Assignee: Nicolet Instrument Corporation, Madison, Wis.

[21] Appl. No.: 85,398

[22] Filed: Aug. 14, 1987

[51] Int. Cl.[4] .............................................. A61B 5/12
[52] U.S. Cl. .................................... 128/746; 128/789
[58] Field of Search ................ 128/746, 789; 381/169, 381/187–188, 205

[56] References Cited

U.S. PATENT DOCUMENTS

| | | | |
|---|---|---|---|
| 915,824 | 3/1909 | Branaman | 128/789 X |
| 1,623,552 | 4/1927 | Pollard | 128/789 |
| 1,684,859 | 9/1928 | Catlin | 128/789 |
| 3,757,769 | 9/1973 | Arguimbau et al. | 128/746 X |
| 3,949,735 | 4/1976 | Klar et al. | 128/746 X |
| 4,014,320 | 3/1977 | Richards | 128/746 |
| 4,025,733 | 5/1977 | Klar et al. | 128/746 X |
| 4,079,198 | 3/1978 | Bennett | 128/746 X |
| 4,201,225 | 5/1980 | Bethea, III et al. | 128/746 |
| 4,289,143 | 9/1981 | Canavesio et al. | 128/746 |
| 4,459,996 | 7/1984 | Teele | 128/746 |

OTHER PUBLICATIONS

F. M. Wiener, et al., "The Pressure Distribution in the Auditory Canal in a Progressive Sound Field", *The Journal of the Acoustical Society of America*, vol. 18, No. 2, Oct. 1946, pp. 401–408.

F. D. McDonald, "Earmold Alteration Effects as Measured in the Human Auditory Meatus", *The Journal of the Acoustical Society of America*, vol. 48, No. 6, Part 2, 1970, pp. 1366–1372.

D. W. Teele et al., "Detection of Middle Ear Effusion by Acoustic Reflectometry", *The Journal of Pediatrics*, vol. 104, No. 6, Jun. 1984, pp. 832–838.

S. Gilman et al., "Acoustics of Ear Canal Measurement of Eardrum SPL in Simulators", *Journal of the Acoustical Society of America*, vol. 80, No. 3, Sep. 1986, pp. 783–793.

K. N. Stevens et al., "Calibration of Ear Canals for Audiometry at High Frequencies", *Journal of the Acoustical Society of America*, vol. 81, No. 2, Feb. 1987, pp. 470–484.

W. J. Murphy et al., "Two Microphone Measurement of Acoustic Intensity in the Ear Canal as a Calibration of High-Frequency Hearing".

Abstract of paper presented May 14, 1987 at the 113th meeting of the Acoustical Society of America, Indianapolis, Ind., and the unpublished notes reporting the content of that presentation.

M. R. Stinson, "Spatial Variation of Phase in Ducts and the Measurement of Acoustic Energy Reflection Coefficients", Journal of the Acoustical Society of America, vol. 77, No. 2, Feb. 1985, pp. 386–393.

M. R. Stinson et al., "Estimation of Acoustical Energy Reflections at the Eardrum from Measurements of Pressure Distribution in the Human Ear Canal", Journal Acoustical Society of America, vol. 72, No. 3, Sep. 1982, pp. 766–773.

*Primary Examiner*—Edward M. Coven
*Assistant Examiner*—Angela D. Sykes
*Attorney, Agent, or Firm*—Lathrop & Clark

[57] ABSTRACT

A mounting apparatus for mounting a microphonic probe tube on a patient includes a headband adapted to fit securely on the head of a patient and an adjusting arm which extends outwardly from the headband above each ear of the patient. Each adjusting arm is mounted to the headband in a manner which allows lateral adjustment of the position of the arm so that it can be located directly over the ear canal. The microphonic probe tube is mounted to a mounting rod extending downwardly from the adjusting arm and can be positioned at a point directly outwardly from the ear canal. When the probe tube is so positioned, a dial at the end of the adjusting arm can be turned by the operator to move the probe tube tip a selected distance into the ear canal of the patient to a position at which the real ear measurements are to be made. The precise position of the probe tube tip within the ear canal can be determined by reading the position of an indicator on the adjusting arm with respect to a scale formed along the arm which shows the relative position of the pendant mounting rod and thus the probe tube tip. The secure mounting of the adjusting arm to the headband and the firm mounting of the headband on the head of the patient allows precision measurements of the probe tube tip position to be made and inadvertent contact of the probe tube with the ear drum to be minimized despite motions of the patient's head.

21 Claims, 2 Drawing Sheets

MICROPHONIC PROBE TUBE MOUNTING FOR REAL EAR MEASUREMENTS

FIELD OF THE INVENTION

This invention pertains generally to the field of apparatus and techniques for the diagnosis of human hearing problems and particularly to the measurement of sound pressures within the ear canal.

BACKGROUND ART

It is often important in the diagnosis and treatment of hearing problems to be able to determine with accuracy the acoustic pressure within the ear canal of a patient or the change in acoustic pressure introduced by a hearing aid. For example, the most accurate analyses of the hearing of a patient can be made by determining the actual sound pressure at the ear drum and relating these physical measurements to a patient's behavorial response. To obtain such physical measurements, it is necessary to provide a relatively nonintrusive means of measuring the pressure at or near the ear drum in a manner that does not substantially affect the transmission of sound through the ear canal. Usually the foregoing measurements are made by inserting a thin probe tube into the ear canal which transmits the sound pressure within the canal at the tip of the tube to an externally located microphone. Positioning of a probe into the ear canal must be made with great care to avoid contact with the ear drum. Precise and repeatable positioning is complicated by patient head and body motions and lack of cooperation in small children.

The measured value of a sound waveform in an open or closed ear canal is highly dependent upon the position of the tip of the sound collection tube, particularly relative to the frequency of the acoustic signal. Therefore, the accuracy and reliability of canal sound pressure level measurements are directly related to the stability and accuracy of the probe tube tip position. A second factor which can influence the absolute value of the measured canal frequency gain is the method by which the pressure is measured. Typically, a comparison is made between a microphone placed external to the canal and a microphone placed within the canal. This two microphone technique results in a differential recording which is very sensitive to placement of the reference microphone. Unfortunately, there is no consensus in the scientific or clinical community as to the "optimal" placement of the reference microphone. Conventional probe tube measurement instruments typically restrict the placement of the reference microphone to a specific location which may not be the location preferred by the user.

SUMMARY OF THE INVENTION

The microphonic probe tube mounting apparatus of the present invention is mountable to the head of a patient to provide a stable reference location relative to the ear of the patient which minimized the effect of voluntary or involuntary movements of the head of the patient. A reference mount for the probe tube is provided adjacent to one or both ears of the patient which allows a probe tube to be inserted into the ear canal and precisely located with respect to any reference point in the canal. In this manner, the insertion of the probe tube into the ear can be done in a way which minimizes the chance of inadverdent contact of the probe tube with the eardrum. Once the tip of the probe tube has been located at a reference point with respect to the ear canal, it can be moved inwardly or outwardly in a straight line a precise, measurable distance so that precise real ear measurements of the sound pressure at chosen locations within the ear canal can be determined efficiently and accurately.

The positioning apparatus includes a headband which is mountable upon a patient's head and can be secured thereon to be held firmly in a fixed position unaffected by motions of the wearer. An adjustable mounting mechanism is attached to the headband on each side thereof just above the position of each ear and has an adjusting arm extending outwardly therefrom. The adjusting arm has a mounting rod which is adapted to engage and hold a microphonic probe tube which extends toward the ear canal. The adjusting arm has a slide screw therein which can be turned to move the mounting rod inwardly and outwardly. The relative position of the mounting rod can be measured with respect to a scale on the arm so that the position of the probe tube tip with respect to a reference point can be determined. The adjusting arm is preferably mounted to the headband so that its lateral position with respect to the patient's head can be selected. Once the desired position has been obtained such that the probe tube tip may be inserted by advancing it in a substantially straight line into the ear canal, the adjusting arm is secured in that position, allowing the adjusting arm to be used to selectively advance the probe tube toward and into the ear canal. Provision is made for mounting a reference microphone to the headband at various positions, or to the adjusting arm, to allow the sound measurements made by the probe microphone to be referenced to the sound detected by the reference. In this manner, it is possible to determine the frequency response of the ear in a reliable manner relative to a reference microphone positioned in accordance with the operator's preference.

Further objects, features, and advantages of the invention will be apparent from the following detailed description when taken in conjunction with the accompanying drawings.

DESCRIPTION OF THE PREFERRED EMBODIMENTS

Figure 1:
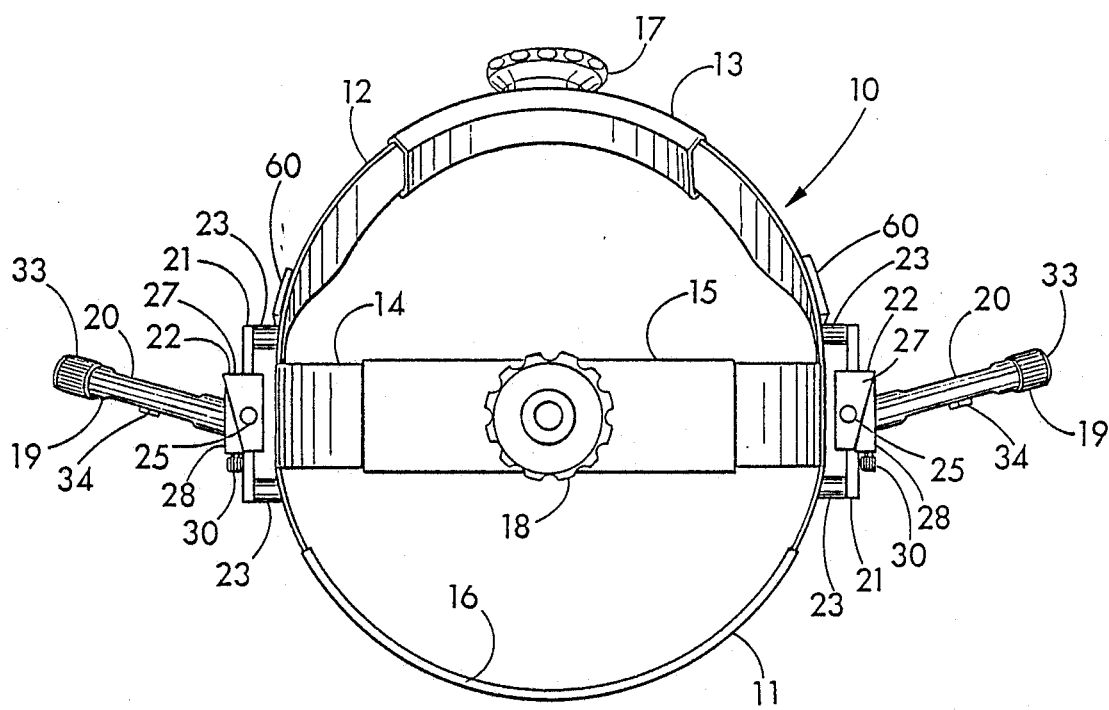
FIG. 1 is a top plan view of apparatus for positioning a microphonic probe tube in accordance with the present invention.

With reference to the drawings, apparatus for positioning a microphonic probe tube in accordance with the present invention is shown generally at 10 in FIG. 1. The apparatus 10 includes a headband 11 adapted to be mounted securely on the head of a patient. To this end, the headband 11 has a lateral strap 12 substantially encircling a patient's head, with a lateral adjusting mechanism 13, and a medial strap 14 attached to an extending from opposite sides of the lateral strap 12, which is itself adjusted by an adjusting mechanism 15. A protective band 16 extends across the front of the lateral strap 12 to fit against the forehead of the patient. In use, the headband 11 is slipped over the top of the head of the patient and the knobs 17 and 18 on the adjusting mechanisms 13 and 15, respectively, are turned to tighten their respective straps so that the headband is held firmly in place on the patient's head. The adjusting mechanisms 13 and 15 may be of standard construction, commonly found on various headband mounted systems, and various other mechanisms well known in the art may also be utilized. The primary requisite of the adjusting mechanism is that they allow a firm fit of the headband on the patient so that the headband will not shift with respect to the patient's head once the headband had been secured in a desired position.

Figure 4:
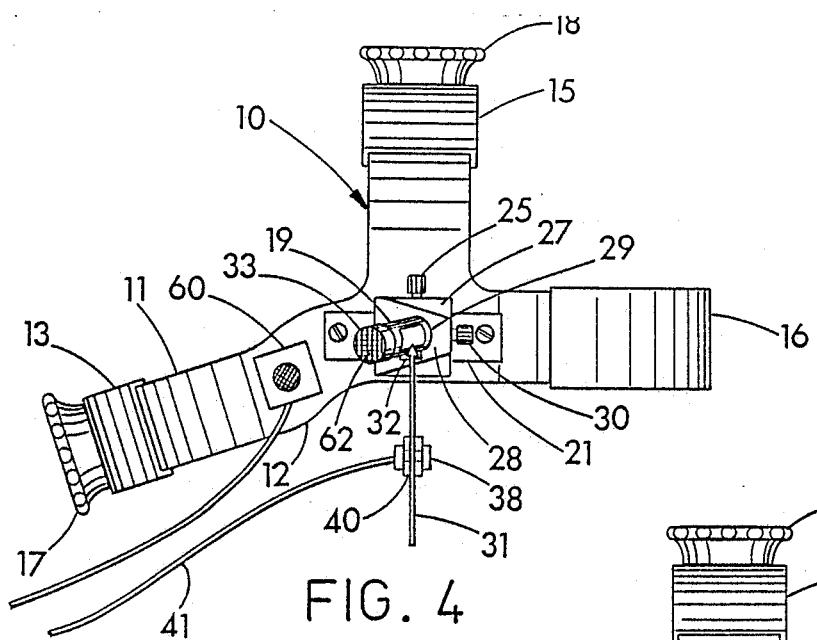
FIG. 4 is a side elevational view taken from the left side of the apparatus of FIG. 1.

Two adjusting arms 19, each having an elongated main housing 20, extend outwardly from opposite sides of the lateral strap portion 12 of the headband and are mounted in a selected position to the headband by a mounting means which includes a slide bar 21 and a mounting slide block 22. The slide bar 21 is secured to the lateral strap 12 by blocks 23 which are riveted or otherwise attached to the strap and to the inner side of the slide bars 21. The slide block 22 fits over the slide bar 21 and can slide back and forth thereon to allow lateral adjustment of the position of the adjusting arms 19. A thum screw 25 on each side block may be tightened to secure the slide block in a desired position. Each slide block 22 is preferably formed in two parts, having a first section 27 which is mounted to slide back and forth on the slide bar 21 and a second section 28, detachable from the first section, which slips into a generally V-shaped channel in the first section, as best shown in FIG. 4. The inner end of the adjusting arm housing 20 fits tightly into a socket 29 in the second section 28 and is secured in position in the socket by a thumb screw 30.

Figure 2:
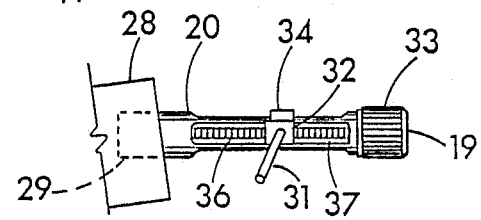
FIG. 2 is a bottom view of an adjusting arm portion of the apparatus of FIG. 1.
Figure 3:
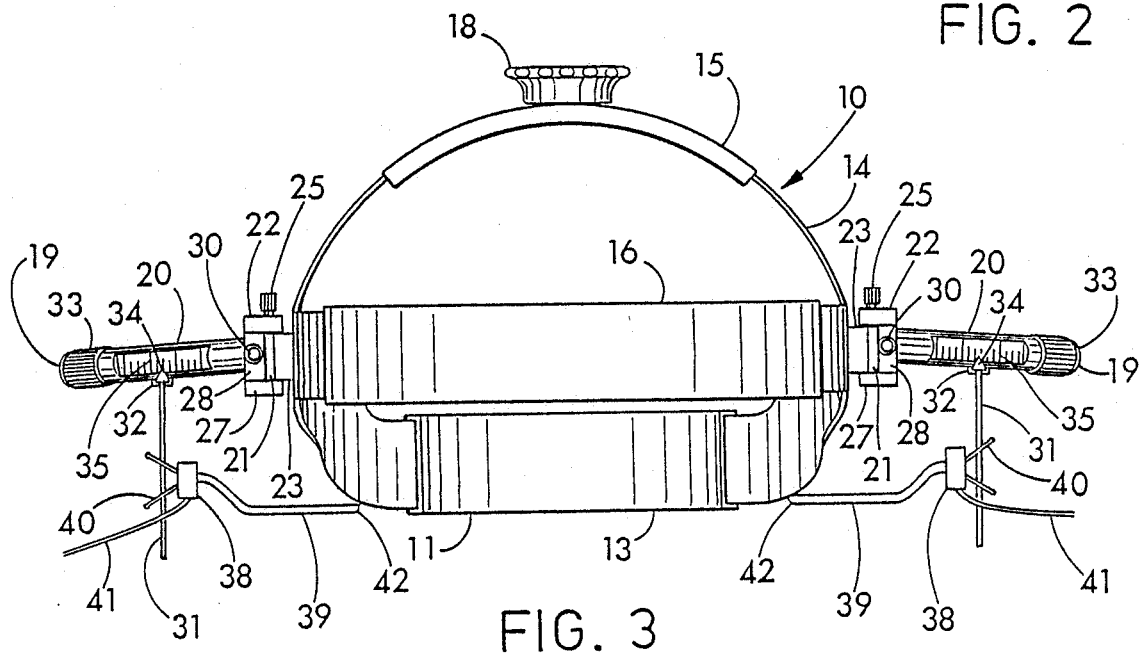
FIG. 3 is a front elevational view of the apparatus of FIG. 1.

Each adjusting arm 19 has a pendant mounting rod 31 extending downwardly therefrom which is attached to a guide 32 which slides back and forth within the arm housing 20. The position of the pendant mounting rod 31 is adjusted by turning a dial 33 at the end of the adjusting arm. The relative position of the mounting rod 31 can be determined by the operator by denoting the position of an indicator 34 with respect to a scale 35 marked on the side of the arm housing 20. As best shown in FIG. 2, a bottom view of the right side adjusting arm 19, the guide 32 is threaded to a rotating screw 36, connected to the dial 33 by which it is rotated, such that the guide 32 will be driven back and forth by the screw 36 as the dial is rotated. The guide 33 is restrained from sideways motion by the edges of a channel 37 formed in the bottom of the arm housing 20. It is understood that the left side adjusting arm 19 and mounting means are the mirror image of but otherwise identical to the right side adjusting arm and mounting means.

A microphone 38 with a hollow plastic probe tube 39 extending from it together form a microphonic probe tube which is mounted to the pendant rod 31 by a spring loaded clip 40 having holes therein through which the rod 31 is passed. The microphone is mounted to receive sound transmitted through the hollow interior of the probe tube. The probe tube 39 is preferably formed of a soft, relatively flexible plastic to minimize discomfort of the patient as the probe tube is inserted into the patient's ear canal. It is apparent that a miniature microphone could be mounted at the tip of the probe tube for insertion into the ear, and forms a microphonic probe tube equivalent to a hollow tube with externally mounted microphone. The operator can adjust the position of the microphone 38 and the probe tube 39 vertically by grasping the two ends of the clip 40 to loosen the clip on the rod, and then moving the clip up or down until the probe tube is at the desired height. When the clip 40 is released, it holds tight in position on the rod 31. Electrical wires 41 extend from the microphone 38 to monitoring equipment (not shown) which records and analyzes the signals picked up by the microphone 38.

In preparation for use of the apparatus on a patient, the operator may remove the arms 19 from the slide blocks by turning the thumb screws 30 to loosen the connection between the slide blocks and the arm housings. The knobs 17 and 18 on the adjusting mechanisms 13 and 15 are then turned to loosen the straps of the headband so that the headband will fit easily over the head of the patient. With the headband on the patient, the knobs 17 and 18 on the adjusting mechanisms 13 and 15 are turned to tighten the headband 11 so that it will be both comfortable to the patient but tightly held on the patient's head so that it will remain fixed with respect to the head despite any movements by the patient. The arms 19 are then placed into the sockets 29 in the slide blocks and secured in place with the thumb screws 30. The position of the pendant rod 31 on each adjusting arm is preferably initially set to be in a fully retracted position such that the mounting rods are as far as possible from the patient's ear. The mounting clips 40, with microphone and probe tube attached, are then slipped on the pendant rods 31. The slide blocks 22 are then moved along the slide bar 21 until the probe tube is aimed substantially down the ear canal. The height of the probe tube with respect to the ear canal may also be adjusted by moving the clips 40 up or down until the probe tube is at the height of the ear canal.

With the probe tube aimed down the ear canal, the slide blocks 22 are secured in place by tightening down the thumb screw 25. At this time, the microphonic probe tube is fixed in a position referenced to the headband and thus to the head of the patient; thus, the position of the probe tube tip 42 with respect to the patient's ear will not significantly change if the patient moves his head. By turning the dial 33 on the end of the adjusting arm, the operator may then advance the tip 42 of the probe tube to a reference point. The ear canal entrance may be utilized as the base line reference position, although other reference positions within the ear canal may also be utilized—for example, a pre-selected distance from the eardrum. Such a reference position with respect to the ear drum may be established by utilizing the probe tube and microphone to determine the sound field pattern within the ear canal. With the reference point determined, the operator may then refer to the position of the indicator 34 with respect to the scale 35 and note the initial or reference position on the scale. Assuming that the operator wishes to take readings at a depth in the ear canal different than the reference point, the operator then may move the probe tube tip in substantially straight line motion by turning the dial 33 until the indicator 34 is moved to another position on the scale which shows a difference in position from the reference position equal to the desired depth of the probe tube within the ear canal. At this point the hearing tests may be started. It is apparent that both ears may be tested in the same sitting or even simultaneously by utilizing the apparatus of the invention in accordance with the above-described procedure for locating the tip of the probe tube within the ear canal.

The probe tubes 39 are preferably relatively flexible and soft for comfort of the patient, but sufficiently stiff so that the tubes do not droop excessively. Thus, with the mounting clips 40 tightly secured to the rods 31, the probe tube tips will be maintained in a fixed position with respect to the adjusting arms 19, which themselves are maintained in a fixed position on the patient's head by the headband 12. This secure location of the probe tube tip despite voluntary or involuntary motions of the patient greatly simplifies the operator's task of moving the probe tube into the ear canal without inadvertently contacting the ear drum. Moreover, the referencing of the probe tube tip to the patient's head without restricting the motion of the patient allows greater flexibility in the administering of audiological measurements than has heretofore been possible, since the patient may turn his head toward or away from a sound source while sound measurements are being made within the ear canal. Measurements may even be made during activities by the patient, for example when the patient is moving around a room. The apparatus may also be utilized to test the operation of hearing aids which are inserted into the ear canal together with the probe tube so that the actual sound levels produced by the hearing aid within the ear canal can be determined.

Figure 5:
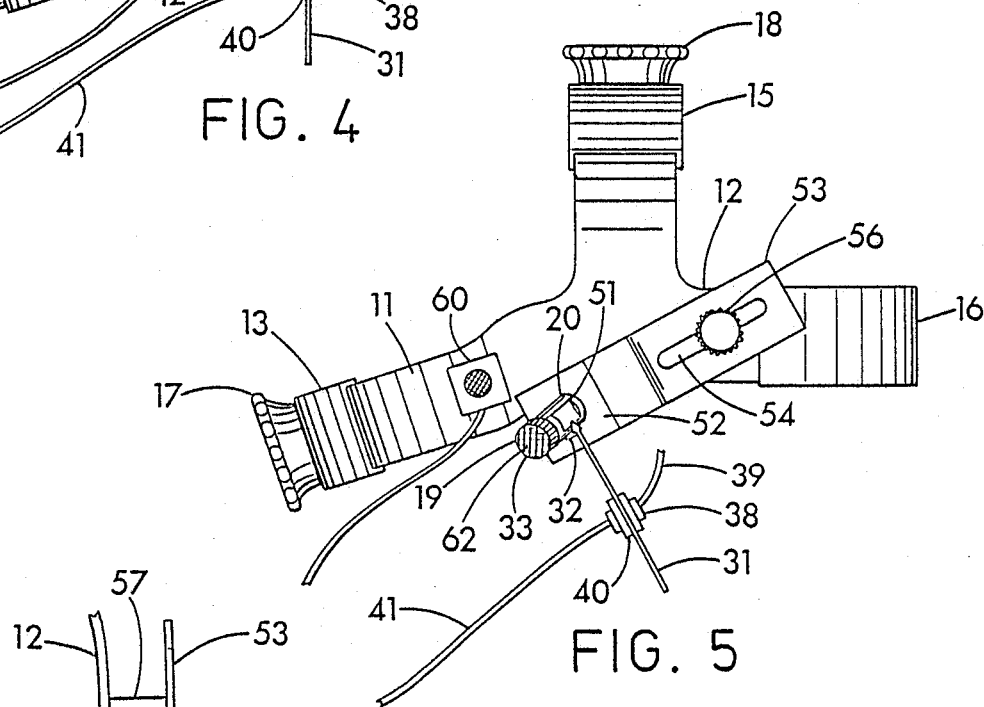
FIG. 5 is a side elevational view of a modified embodiment of apparatus in accordance with the present invention.
Figure 6:
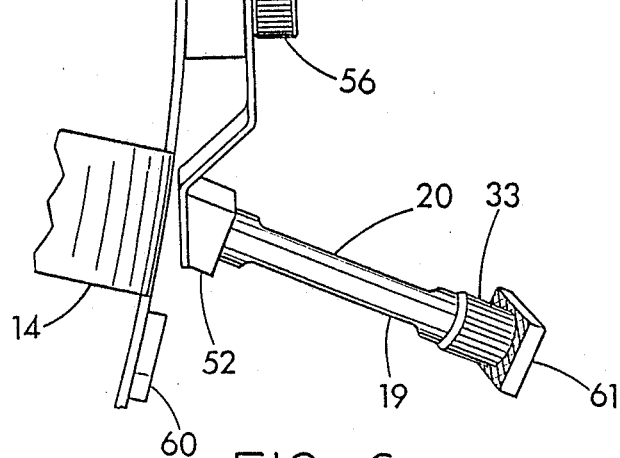
FIG. 6 is a top view of a portion of the apparatus of FIG. 5, showing the mounting of the adjusting arm.

An embodiment of the apparatus of the invention having an alternative means for mounting the adjustable arm 19 to the headband 11 is shown in FIGS. 5 and 6. Each adjustable arm 19 and the headband 11 are identical in construction to the corresponding structures of FIGS. 1-4. The arm 19 is inserted into a socket 51 in a mounting block 52 attached to one end of a mounting plate 53. The plate 53 has a slot 54 therein extending lengthwise in the plate. An adjusting thumb screw 56 has a threaded portion passing through the slot 54 into engagement with a threaded hole (not shown) in a block 57 attached to the side of the headband lateral strap 12. To adjust the relative position of the adjustable arm 19 laterally, as well as vertically, the operator loosens the screw 56 and moves the plate 53 so that the screw 56 slides in the slot 54, or pivots the plate about the screw 56, until the arm 19 is in the desired position—that is, until the probe tube 39 is directly aimed at the opening of the ear canal. At this position, the operator tightens the thumb screw 56, which presses against the side of the plate 53 to hold the plate and thus the adjustment arm 19 firmly in place. The insertion of the probe tube 39 into the ear canal may then be carried out by turning the dial 33 on the adjustable arm as described above. It is, of course, understood that a similar, mirror image mounting structure is formed on the opposite side of the headband for placement of the probe tube at the opposite ear of the patient.

An additional advantage of the mounting apparatus of the present invention is that it allows a reference microphone to be mounted in a fixed position with respect to the patient's head, so that the actual sound being received by the patient's ear can be measured despite head movements. For example, a reference microphone 60 can be attached to the headband strap 12 at a position as illustrated in FIGS. 1 and 4-6 which will be right behind the patient's ear. This is the preferred position for determining the sound picked up by a behind-the-ear hearing aid where tests are to be made on a patient wearing such an aid. As an alternative example, a reference microphone 61 may be mounted on the end of the dial portion 33 of the adjustment arm 19, as shown in FIG. 6, which is the preferred mounting position if no hearing aid is present and it is desired to measure the sound being received at the patient's external ear. The reference microphones, which are small and light, can readily be fitted so they can be attached at one of several positions on the headband or on the adjusting arm—for example, by using Velcro (TM) type hook and loop fasteners. Attachment pads for such fasteners are illustrated at 62 in FIGS. 4 and 5. Because the apparatus provides many such positions where a reference microphone may be attached, all maintained in fixed relation to the head of the patient, a variety of sound response transfer functions can be obtained by referencing the response at the probe tube microphone to the reference microphone positioned at each of its possible locations. Thus, the clinician now is able to select the frequency response which is most appropriate.

It is understood that the invention is not confined to the particular construction and arrangement of parts herein illustrated and described, but embraces such modified forms thereof as come within the scope of the following claims.

What is claimed is:

1. Microphone probe tube mounting apparatus for real ear measurements comprising:
   (a) headband means for selectively mounting securely to the head of a patient;
   (b) an elongated microphonic probe tube having a tip and adapted to extend into an ear canal without contacting the ear canal;
   (c) adjusting arm means for holding the microphonic probe tube and for allowing the user to advance and retract the microphonic probe tube into and out of the ear canal of the patient in a substantially straight line;
   (d) means for mounting the adjusting arm means to the headband means such that the probe tube is referenced in position to the headband means; and
   (e) means, mounted on the adjusting arm means, for indicating the distance that the probe tube has been advanced or retracted.

2. The apparatus of claim 1 wherein the headband means includes lateral and medial straps and means thereon for tightening the straps on the head of the patient to hold the headband means tightly in place so that it does not move with respect to the head during movements by the patient.

3. The apparatus of claim 1 wherein the adjusting arm means includes an arm housing having an outer end, a dial mounted on the outer end of the housing and connected to a threaded screw running through the housing, a guide threaded to the screw to move back and forth in the housing, a mounting rod extending from the guide, and a clip on the mounting rod attached to the microphonic probe tube to hold the same in position on the mounting rod.

4. The apparatus of claim 3 wherein the means for indicating the distance the probe tube has been advanced or retracted which is mounted on the adjusting arm means includes a scale of position markings along the outside of the housing and an indicator connected to the guide to move back and forth with the guide and point to the markings on the scale to allow the operator to determine the position of the guide and thereby the position of the tip of the microphonic probe tube.

5. The apparatus of claim 1 wherein the means for indicating the distance the probe tube has been advanced or retracted which is mounted on the adjusting arm means includes an arm housing having a scale of position markings on the side thereof and an indicator movable along the scale and connected to move with the microphonic probe tube so that the operator can determine the relative position of the probe tube tip.

6. The apparatus of claim 1 wherein the headband means includes a lateral strap portion adapted to extend around the head of the patient, wherein the adjusting arm means includes an elongated housing, and wherein the means for mounting the adjusting arm means to the headband includes a slide bar extending laterally along the side of the headband lateral strap and attached to the lateral strap, a slide block slidable back and forth on the slide bar, a thumb screw threaded through the slide block to releasably engange the slide bar to hold the slide block when the screw is engaged to the slide bar in a selected position, and a socket in the slide block into which an end of the adjusting arm housing is inserted.

7. The apparatus of claim 1 wherein the headband means includes a lateral strap portion adapted to extend around the head of the patient, wherein the adjusting arm means includes an elongated housing, and wherein the means for mounting the adjusting arm means to the headband means includes an elongated plate having a slot therein extending partially along the length thereof, a block portion having a socket into which an end of the housing of the adjusting arm means is inserted to be held therein, and a mounting thumb screw extendiang through the slot in the plate and threaded into the lateral strap to adjustably hold the plate in a desired position on the headband means, whereby the plate can be rotated about the mounting screw when it is loosened and be moved back and forth with respect to the mounting screw within the slot in the plate.

8. The apparatus of claim 1 wherein the headband means has a left side and a ride side and there are two adjusting arm means and wherein the means for mounting the adjusting arm to the headband means mounts one adjustable arm means on the left side of the headband means and one adjustable arm means on the right side of the headband means such that measurements can be taken on both the left and right ears of a patient.

9. The apparatus of claim 1 wherein the microphonic probe tube comprises a hollow plastic tube and a microphone mounted to the end of the tube opposite the tip to receive the sound transmitted through the tube from the tip.

10. The apparatus of claim 1 including a reference microphone and means for mounting the reference microphone so it is held in a fixed position with respect to the headband means.

11. The apparatus of claim 10 wherein the headbeand has a left side and a right side and there are two adjusting arms and wherein the means for mounting the adjusting arm to the headband means mounts one adjusting arm on the left side of the headband means and one adjusting arm on the right side of the headband means such that the measurements can be taken on both the left and right ears of a patient.

12. Microphone probe tube mounting apparatus for real ear measurements comprising:

(a) a headband adapted to securely fit on the head of a patient and having a lateral strap adapted to substantially encircle a patient's head;
(b) a microphonic probe tube extending to a tip;
(c) an adjusting arm having an elongated housing, an inner channel in the housing in which a threaded screw is mounted, an adjusting dial mounted on an outer end of the adjusting arm housing and connected to the screw, a guide within the channel of the arm housing in threaded engagement with the screw therein to be driven back and forth as the dial is turned to rotate the screw, and a pendant mounting rod attached to the guide and extending therefrom, the microphonic probe tube attached to the pendant mounting rod;
(d) means for mounting the adjusting arm to the headband with the adjusting arm extending substantially outwardly from the headband to allow selective lateral positioning of the adjusting arm with respect to the headband; and
(e) means, mounted on the adjusting arm, for indicating the distance that the pendant mounding rod and probe tube have been advanced or retracted.

13. The apparatus of claim 12 wherein the adjusting arm includes a clip on the mounting rod attached to the microphonic probe tube to hold the same in position on the mounting rod.

14. The apparatus of claim 12 wherein the means for indicating the distance the mounting rod and probe tube have been advanced or retracted which is mounted on the adjusting arm includes a scale of position markings along the outside of the housing and an indicator connectred to the guide to move back and forth with the guide and point to the markings on the scale to allow the operator to determine the position of the guide and thereby the relative position of the tip of the microphonic probe tube.

15. The apparatus of claim 12 wherein the means for mounting the adjusting arm to the headband includes a slide bar extending laterally along the side of the headband lateral strap and attached to the lateral strap, a slide block slidable back and forth on the slide bar, a thumb screw threaded through the slide block to releasably engage the slide bar to hold the slide block in a selected position, and a socket in the slide block into which an end of the adjusting arm housing is inserted.

16. The apparatus of claim 12 wherein the means for mounting the adjusting arm to the headband includes an elongated plate having a slot therein extending partially along the length thereof, a block portion having a socket into which an end of the housing of the adjusting arm means is inserted to be held therein, and a mounting thumb screw extending through the slot in the plate and threaded into the lateral strap to adjustably hold the plate in a desired position on the headband, whereby the plate can be rotated about the mounting screw when it is loosened and be moved back and forth with respect to the mounting screw within the slot in the plate.

17. The apparatus of claim 12 wherein the microphonic probe tube comprises a hollow plastic tube and a microphone mounted to the end of the tube opposite the tip to receive the sound transmitted through the tube.

18. The apparatus of claim 12 including a reference microphone and means for mounting the reference microphone in a fixed position with respect to the headband.

19. A method for making real ear measurements comprising the steps of:
 (a) mounting a headband securely on a patient's head;
 (b) positioning a microphonic probe tube having a tip so that its tip is directly outwardly from the ear canal of the patient and holding the probe tube referenced to the headband in that position so that it can only move inwardly toward the ear canal or outwardly therefrom; and
 (c) advancing the probe tube into the ear while indicating the distance that the probe tube has been advanced so that the probe tube tip is a known distance from the entrance to the ear canal.

20. The method of claim 19 including the step of receiving sound at a microphone connected to the microphonic probe tube with the tip of the probe tube in the ear canal of the patient.

21. The method of claim 20 including the additional step of positioning a reference microphone at a selected position near the ear canal of the patient which is held in a fixed position with respect to the headband.

* * * * *